United States Patent
Courtney

(10) Patent No.: US 9,039,626 B2
(45) Date of Patent: May 26, 2015

(54) MEDICAL DEVICE WITH MEANS TO IMPROVE TRANSMISSION OF TORQUE ALONG A ROTATIONAL DRIVE SHAFT

(75) Inventor: Brian Kent Courtney, Toronto (CA)

(73) Assignee: SUNNYBROOK HEALTH SCIENCES CENTRE, Toronto, ON (CA)

( * ) Notice: Subject to any disclaimer, the term of this patent is extended or adjusted under 35 U.S.C. 154(b) by 678 days.

(21) Appl. No.: 12/751,800

(22) Filed: Mar. 31, 2010

(65) Prior Publication Data

US 2010/0249601 A1  Sep. 30, 2010

Related U.S. Application Data

(60) Provisional application No. 61/202,742, filed on Mar. 31, 2009.

(51) Int. Cl.
| | |
|---|---|
| A61B 5/00 | (2006.01) |
| A61B 18/18 | (2006.01) |
| A61B 5/02 | (2006.01) |
| A61B 8/12 | (2006.01) |
| A61B 8/00 | (2006.01) |
| A61B 1/00 | (2006.01) |
| A61B 8/08 | (2006.01) |
| A61B 18/14 | (2006.01) |

(52) U.S. Cl.
CPC ........... *A61B 18/18* (2013.01); *A61B 5/6852* (2013.01); *A61B 1/00096* (2013.01); *A61B 1/00172* (2013.01); *A61B 5/0066* (2013.01); *A61B 5/0084* (2013.01); *A61B 5/02007* (2013.01); *A61B 8/0883* (2013.01); *A61B 8/0891* (2013.01); *A61B 8/12* (2013.01); *A61B 8/4461* (2013.01); *A61B 8/543* (2013.01); *A61B 18/1492* (2013.01); *A61B 8/445* (2013.01)

(58) Field of Classification Search
USPC .......................................... 600/462, 459, 466
See application file for complete search history.

(56) References Cited

U.S. PATENT DOCUMENTS

| | | | |
|---|---|---|---|
| 4,681,092 A * | 7/1987 | Cho et al. ..................... 600/18 |
| 4,794,931 A | 1/1989 | Yock | |
| 4,951,677 A | 8/1990 | Crowley | |
| 5,375,602 A | 12/1994 | Lance | |
| 5,429,136 A | 7/1995 | Milo | |
| 5,606,975 A | 3/1997 | Liang | |
| 5,651,366 A | 7/1997 | Liang | |

(Continued)

FOREIGN PATENT DOCUMENTS

| | | |
|---|---|---|
| WO | WO/03/067526 | 8/2003 |
| WO | WO 2004/010856 | 2/2004 |
| WO | WO 2004/096049 | 11/2004 |

OTHER PUBLICATIONS

Harm Ten Hoff "scanning mechanisms for intravascular ultrasounds imaging: a flexible approach"1993, H ten Hoff. Rotterdam, The Netherlands.

*Primary Examiner* — Vani Gupta
(74) *Attorney, Agent, or Firm* — Lynn C. Schumacher; Stephen W. Leonard; Hill & Schumacher

(57) ABSTRACT

The present invention provides minimally invasive imaging probe/medical device having a frictional element integrated therewith for reducing non-uniform rotational distortion near the distal end of a medical device, such as an imaging probe which undergoes rotational movement during scanning of surrounding tissue in bodily lumens and cavities.

23 Claims, 9 Drawing Sheets

(56) References Cited

U.S. PATENT DOCUMENTS

| | | |
|---|---|---|
| 6,110,121 A | 8/2000 | Lenker |
| 6,241,703 B1 * | 6/2001 | Levin et al. ............ 604/22 |
| 6,485,413 B1 | 11/2002 | Boppart |
| 6,544,231 B1 * | 4/2003 | Palmer et al. ............ 604/165.01 |
| 6,592,526 B1 | 7/2003 | Lenker |
| 2007/0161893 A1 | 7/2007 | Milner et al. |
| 2008/0177138 A1 | 7/2008 | Courtney et al. |
| 2009/0018393 A1 * | 1/2009 | Dick et al. ............ 600/109 |
| 2009/0264768 A1 | 10/2009 | Courtney et al. |

* cited by examiner

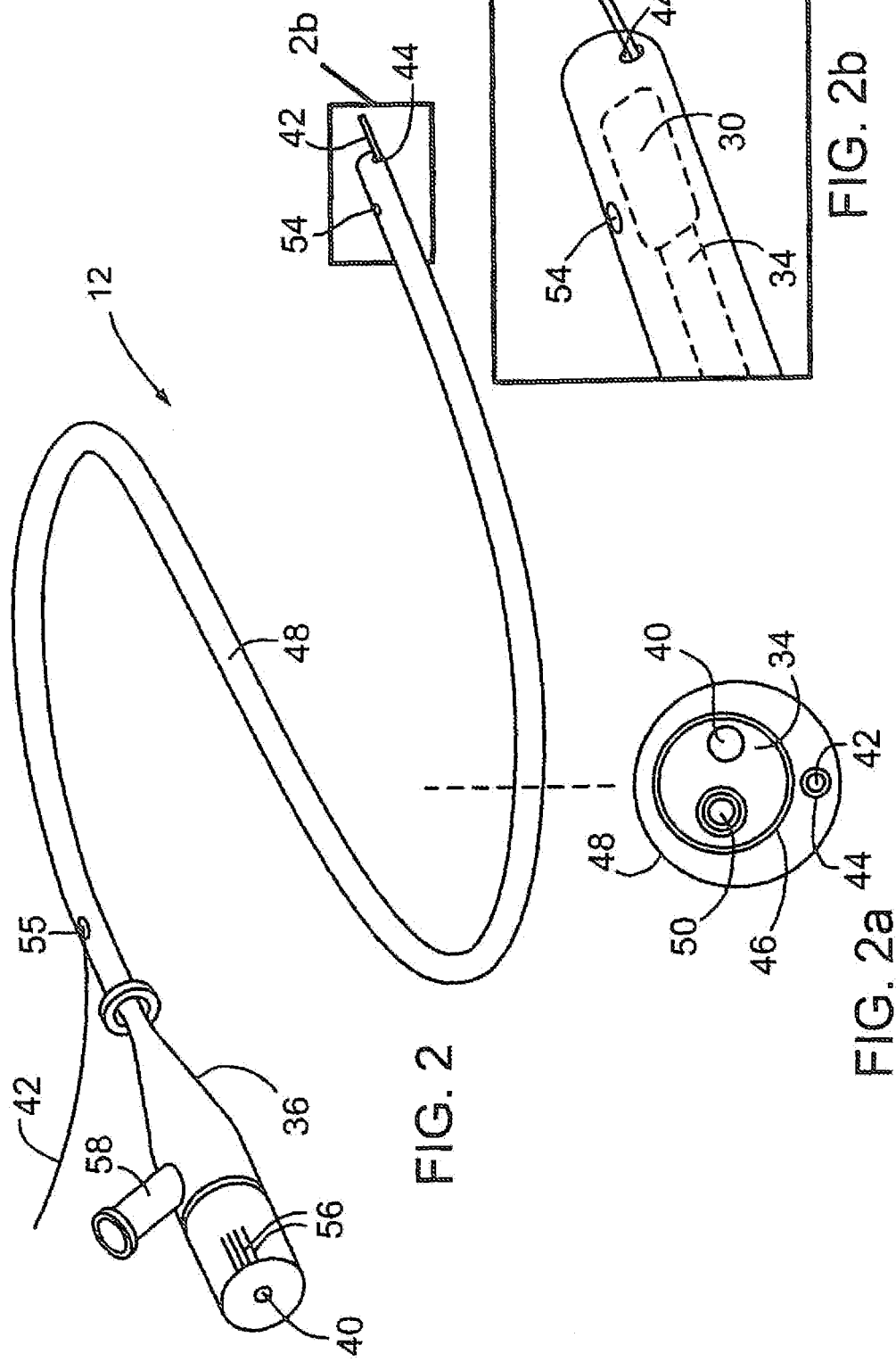

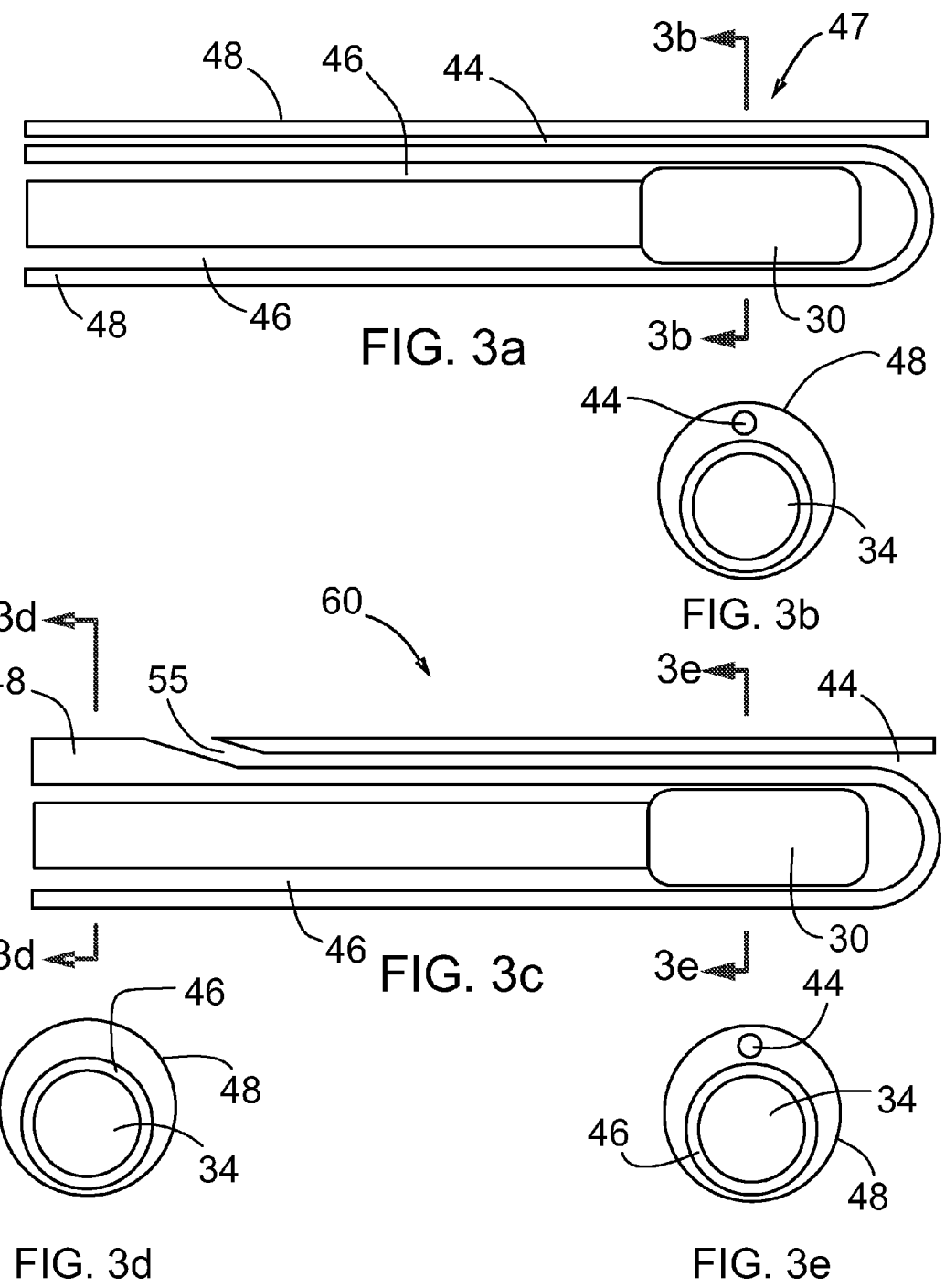

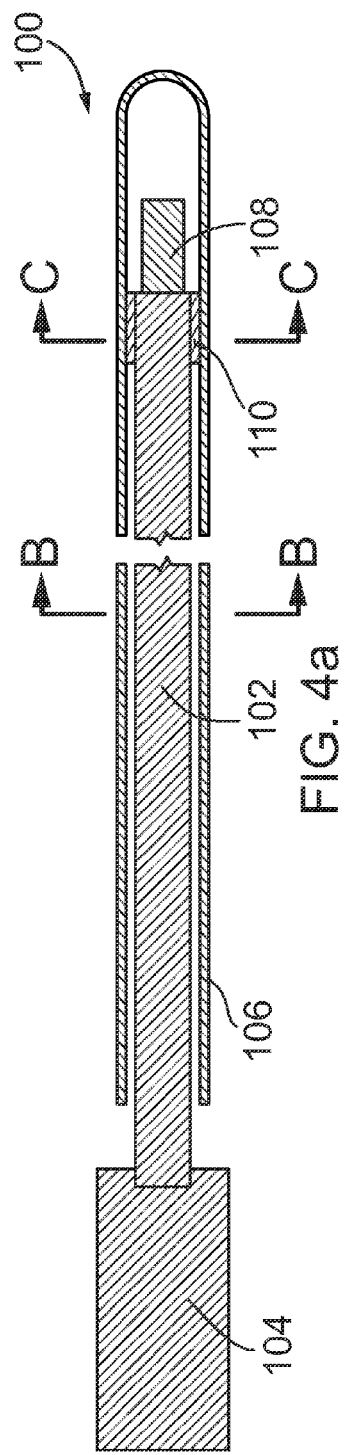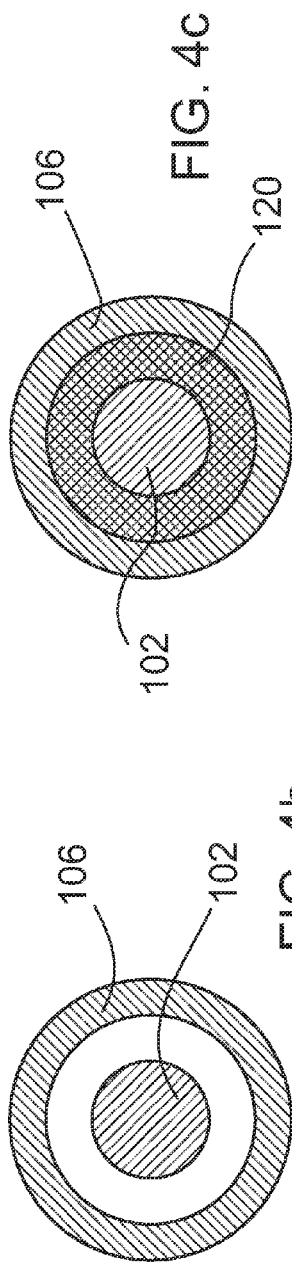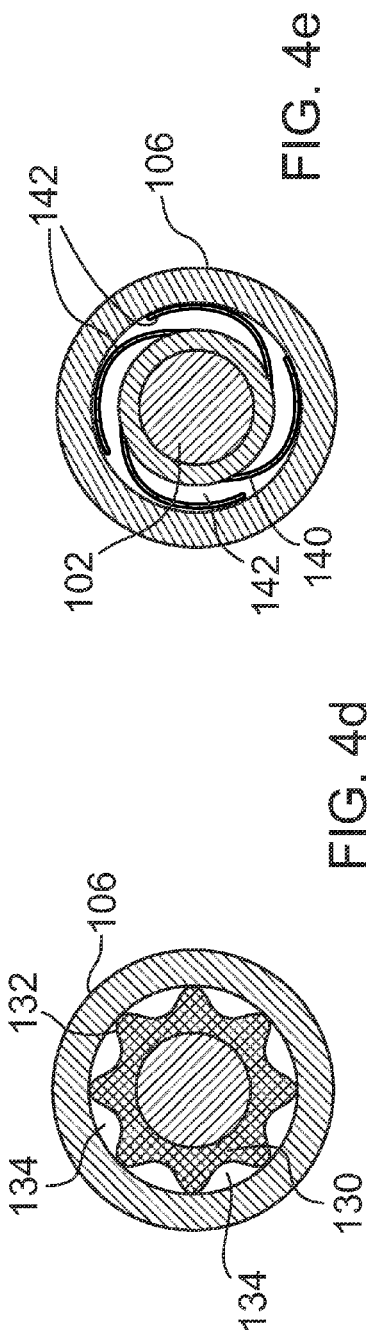

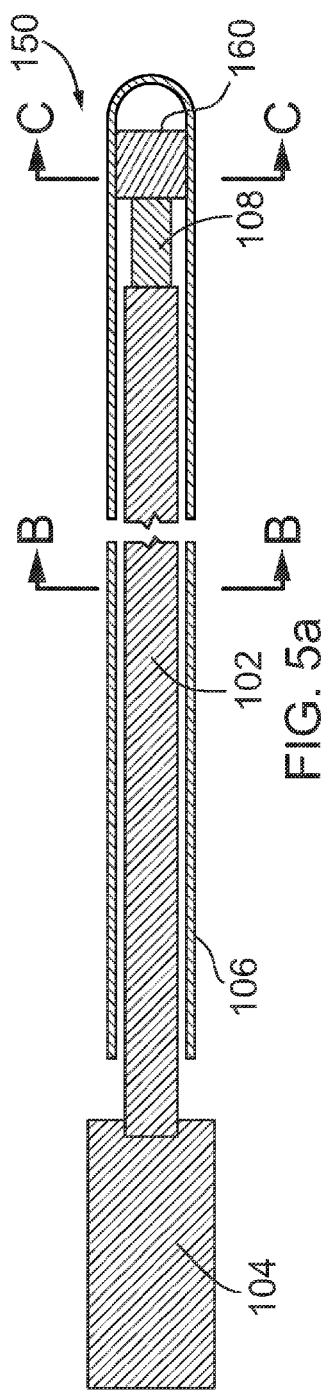
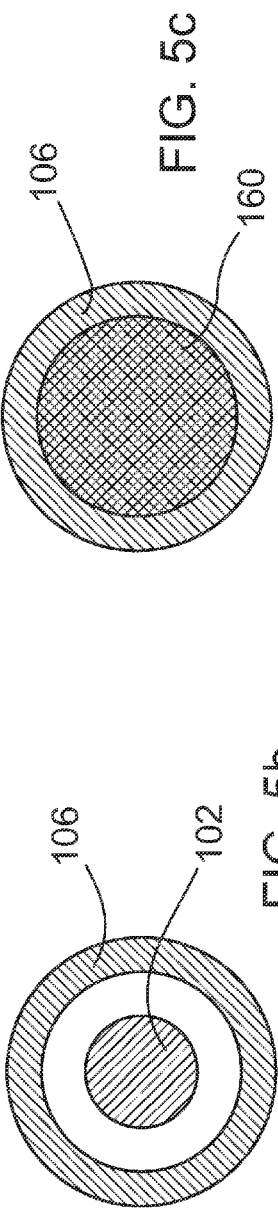
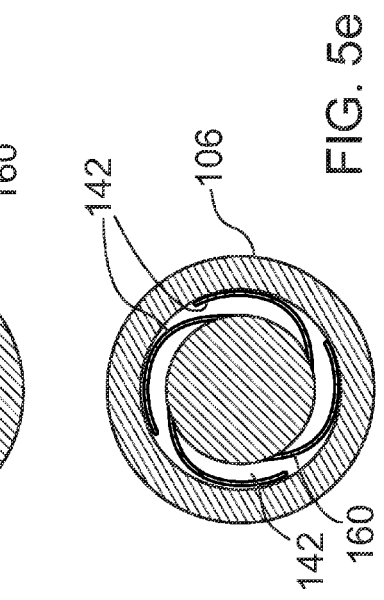
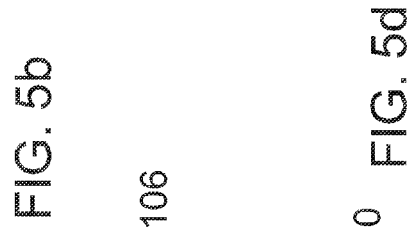
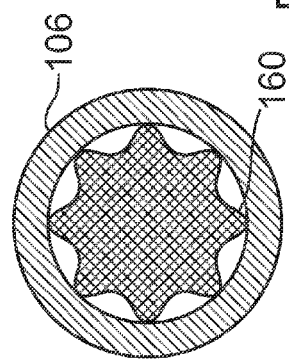

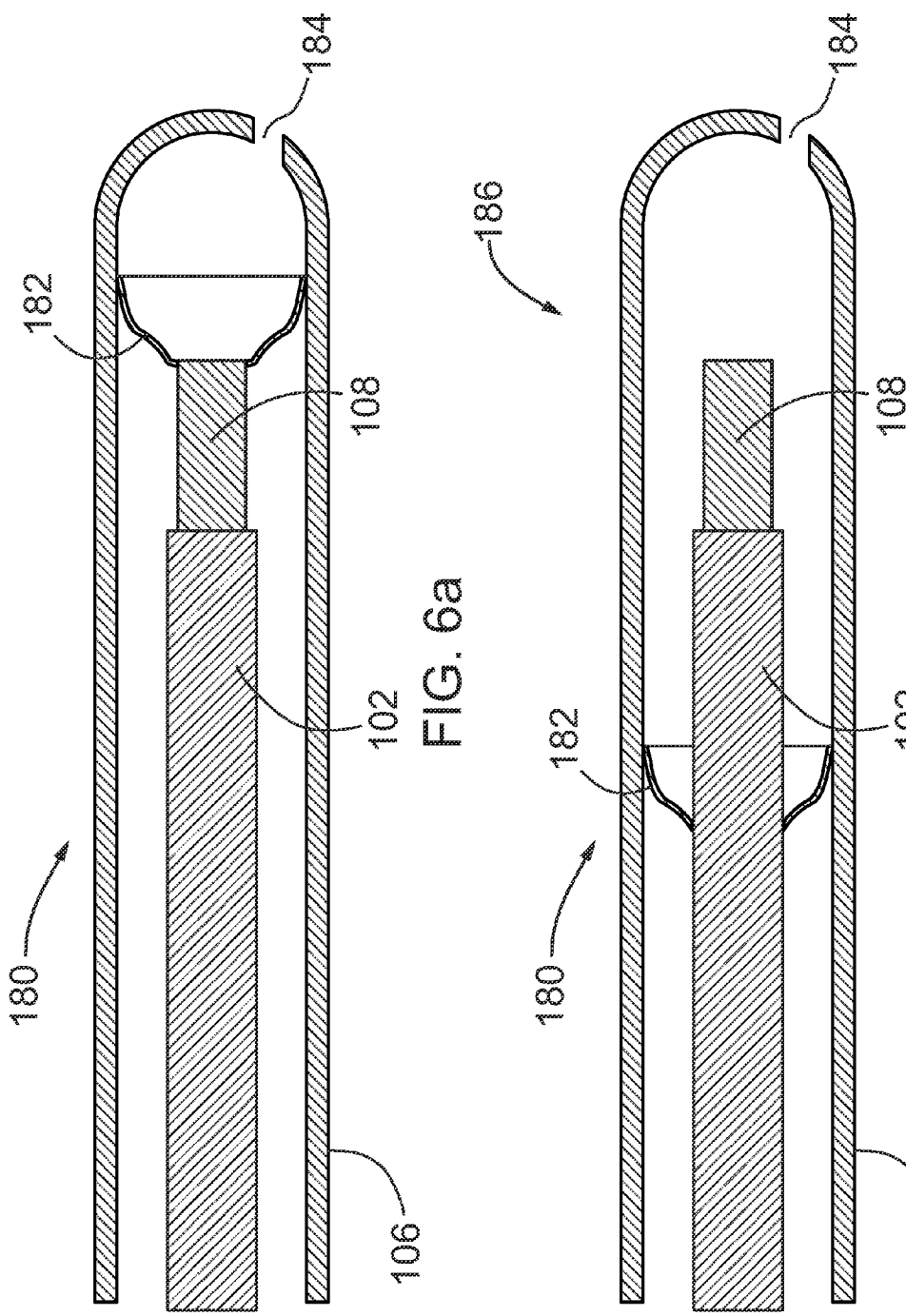

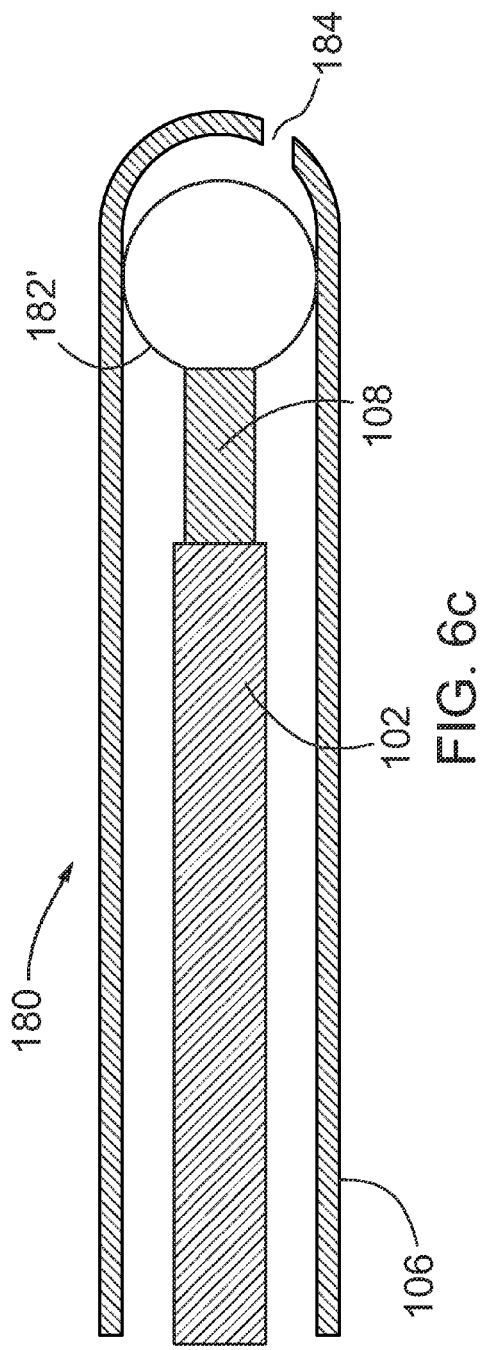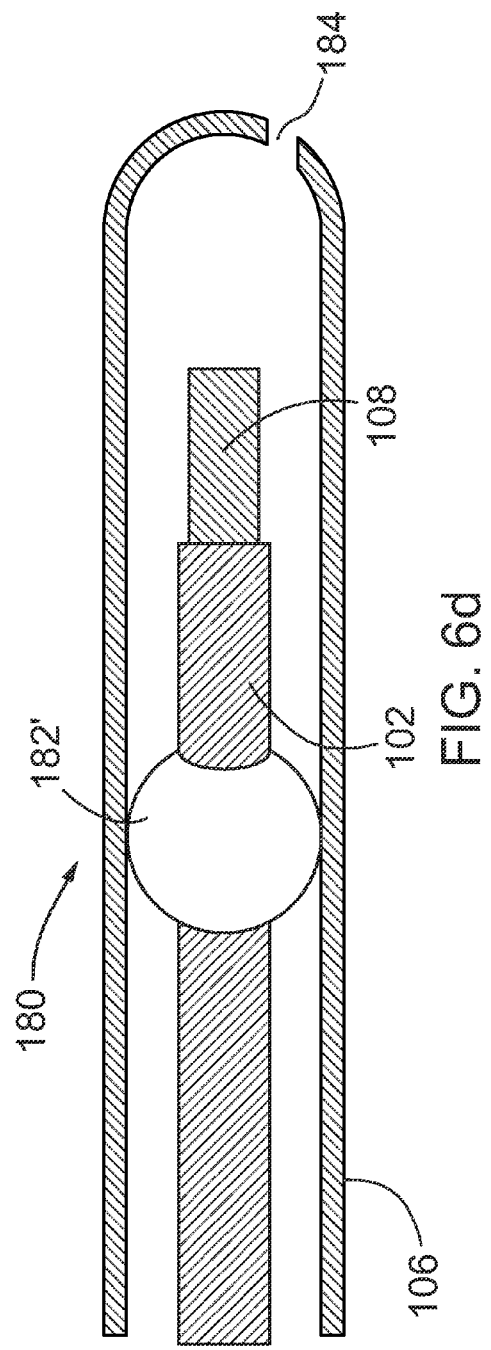

MEDICAL DEVICE WITH MEANS TO IMPROVE TRANSMISSION OF TORQUE ALONG A ROTATIONAL DRIVE SHAFT

CROSS-REFERENCE TO RELATED APPLICATION

This application claims priority to U.S. Provisional Application No. 61/202,742, filed on Mar. 31, 2009, the entire contents of which are incorporated herein by reference.

FIELD OF THE INVENTION

The present invention relates generally to the field of minimally invasive medical devices, including imaging devices for imaging mammalian tissues and structures using high frequency ultrasound, such as intravascular ultrasound (IVUS) and optical imaging methods such as optical coherence tomography (OCT) which incorporate friction devices to improve transmission of torque along a rotational drive shaft.

BACKGROUND OF THE INVENTION

High resolution imaging of the interior of the body (or for dermatologic or opthalmology applications not restricted to the interior) serves multiple purposes, including any of i) assessing tissue structures and anatomy; ii) planning and/or guiding interventions on localized regions of the body; and iii) assessing the result of interventions that alter the structure, composition or other properties of the localized region. High resolution imaging in this particular case refers to high frequency ultrasound and optical imaging methods. For the purposes of this invention, high frequency ultrasound typically refers to imaging with frequencies of greater than 3 MHz, and more typically in the range of 9 to 100 MHz.

High frequency ultrasound is very useful for intravascular and intracardiac procedures. For these applications, the ultrasound transducers are incorporated into a catheter or other device that can be inserted into the body. By way of example, two particularly important implementations of high frequency ultrasound are intravascular ultrasound (IVUS) for imaging blood vessels, and intracardiac echocardiography (ICE) for imaging cardiac chambers. Both ICE and IVUS are minimally invasive, and involve placing one or more ultrasound transducers inside a blood vessel or cardiac chamber to take high quality images of these structures.

Optical imaging methods based on fiber optic technology used in the field of medicine include optical coherence tomography (OCT), angioscopy, near infrared spectroscopy, Raman spectroscopy and fluorescence spectroscopy. These modalities typically require the use of one or more optical fibers to transmit light energy along a shaft between an imaging site and an imaging detector. Optical coherence tomography is an optical analog of ultrasound, and provides imaging resolutions on the order of 1 to 30 microns, but does not penetrate as deeply into tissue as ultrasound in most cases. Fiber optics can also be used to deliver energy for therapeutic maneuvers such as laser ablation of tissue and photodynamic therapy.

Additional forms of imaging related to this invention include angioscopy, endoscopy and other similar imaging mechanisms that involve imaging a site inside the patient using a probe to take pictures based on the back-reflection of light.

High resolution imaging means have been implemented in many forms for assessing several different regions of mammalian anatomy, including the gastrointestinal system, the cardiovascular system (including coronary, peripheral and neurological vasculature), skin, eyes (including the retina), the genitourinary systems, breast tissue, liver tissue and many others. By way of example, imaging of the cardiovascular system with high frequency ultrasound or optical coherence tomography has been developed for assessing the structure and composition of arterial plaque.

High-resolution imaging has been used to measure vessel or plaque geometry, blood flow through diseased arteries, the effect of interventions on arterial plaque (such as by atherectomy, angioplasty and/or stenting). Attempts have also been made using high resolution imaging to identify vascular lesions that have not led to clinical symptoms, but are at increased risk of rupturing or eroding and causing an acute myocardial infarction. These so-called "vulnerable plaques" are an area of interest as the prospect of treating such plaques to pre-empt adverse clinical events is conceptually appealing.

Chronic total occlusions are a specific subset of vascular lesions where the entire lumen of the vessel has been occluded (based on the angiographic appearance of the lesion) for over approximately one month. Most intravascular imaging modalities are "side-viewing" and require passage of an intravascular imaging device through a lesion. In order to image chronic total occlusions, methods of high resolution imaging would be more useful if they were adapted to a "forward-looking" rather than "side-viewing" configuration.

Several of these high resolution imaging means are dependent on the use of a rotary shaft to transmit torque to an imaging device near the distal end of the probe. These rotary shafts are often long, thin and flexible, such that they can be delivered through anatomical conduits, such as the vasculature, genitourinary tracts, respiratory tracts and other such bodily lumens. Ideally, when a torque is applied to the cable in a specified direction the torque cable develops a property of having a close relation between the degree of rotation at its proximal and distal ends. This allows the simplification of the design of the ultrasound catheter by making the angle of rotation at the distal end of the torque cable (within the body) a reasonable approximation of the angle of rotation at the proximal end of the torque cable (outside of the body).

The rotation of the torque cable or shaft at the point from which the imaging occurs may not be identical to the rotation that occurs at the proximal end of the torque cable or shaft. This occurs especially when the flexible shaft is delivered through tortuous passageways and is, at least in part, due to inertia and variable friction between the rotating components and stationary components of the imaging shaft. The assumption that the rotational speeds of the proximal and distal ends of the rotary shaft are equal to each other is also less likely to be valid if the rotational speed varies over time. The undesirable result of not knowing the true angular velocity of the imaging probe at the point from which the imaging beam is directed towards the tissue leads to an artifact referred to as non-uniform rotational distortion (NURD). NURD can lead to significant distortion of the image and a concomitant reduction in the geometric accuracy of the image. Reduction of NURD can improve the geometric accuracy of an image. NURD reduction can also help improve the accuracy of co-registration of images when more than one imaging modality is implemented on the imaging probe (such as combined ultrasound and optical imaging). Further details of various combined acoustic/optical devices which may be used with the NURD reduction mechanisms disclosed herein are disclosed in pending application Ser. No. 12/010,208, entitled IMAGING PROBE WITH COMBINED ULTRASOUND AND OPTICAL MEANS OF IMAGING, which is incorporated herein by reference in its entirety.

NURD reduction can also help improve the accuracy of determining other effects that are dependent on the speed of the imaging assembly or distal end of the rotary shaft. For example, certain 3D scanning mechanisms implemented on imaging probes can be dependent on the true rotational velocity near the distal end of the rotary shaft. Improved predictability of this velocity would be helpful in estimating the scanning pattern of the scanning mechanism, thereby improving the accuracy of reconstruction of 3D imaging data. The rotational drive shaft mechanisms disclosed herein may be integrated into probes using any of the scanning mechanisms disclosed in pending application Ser. No. 12/010,206, entitled SCANNING MECHANISMS FOR IMAGING PROBE, which is incorporated herein by reference in its entirety.

Several other devices in minimally invasive procedures would also potentially benefit from the ability to more accurately measure or estimate rotational motion. Such devices would include atherectomy catheters, such as rotational atherectomy catheters, energy delivery catheters (such as those that deliver laser, radioactive, ablative radiofrequency or acoustic energy), and other catheters that inject, cut, palpate, sense or otherwise manipulate tissue in a directed fashion where more precise control of the rotational motion of a device component at a remote site would be helpful.

SUMMARY OF RELATED ART

A catheter-based system for intravascular ultrasound is described by Yock (U.S. Pat. No. 4,794,931) to provide high resolution imaging of structures in blood vessels. This system comprises an outer sheath, within which there is an ultrasound transducer near the distal end of a long torque cable. When a motor rotates the torque cable and ultrasound transducer assembly, 2D cross-sectional images of anatomical structures, such as blood vessels, can be made. Linear translation of the catheter or the torque cable and ultrasound transducer in combination with the rotational motion of the ultrasound transducer allows for acquisition of a series of 2D images along the length of the catheter.

Milo et al (U.S. Pat. No. 5,429,136) and Lenker et al (U.S. Pat. Nos. 6,110,121 and 6,592,526) describe reciprocating and vibrating means for scanning an ultrasound imaging beam in circumferential or longitudinal directions at the end of the catheter. Reciprocating or vibrating means obviates the need to use a mechanism such as a slip ring to provide an electrical connection to a probe that rotates more than a few rotations in a particular direction, such as more than one or two rotations. Similarly, certain implementations of optical imaging can avoid the use of optical rotary joints using reciprocating or vibrating means.

Liang et al. (U.S. Pat. Nos. 5,606,975 and 5,651,366) describe means of implementing forward-looking intravascular ultrasound where ultrasound is directed towards a mirror with a fixed tilt that causes the ultrasound beam to scan a surface ahead of the probe. The surface scanned approaches the shape of a curved plane, and the resultant shape results from relative rotational motion between the ultrasound transducer and the mirror.

Boppart et al (U.S. Pat. No. 6,485,413) describe several embodiments of optical coherence tomography imaging, including forward looking implementations.

The use of intravascular ultrasound (IVUS) has become commonplace, with many improvements and adaptations to the technology. A flexible torque cable (Crowley, U.S. Pat. No. 4,951,677) improves the fidelity of the transmission of rotational torque along the length of an IVUS catheter, minimizing non-uniform rotational distortion. Despite the use of features disclosed in U.S. Pat. No. 4,951,677, non-uniform rotational distortion remains a common source of undesired artifact in intravascular imaging.

Other approaches that have been considered for minimizing NURD include adding a viscous fluid near the distal end of a rotating conduit (Peterson PCT Application US2003/023019), using an imaging catheter that vibrates across a small range of angles rather than continuous rotation (Lenker U.S. Pat. Nos. 6,110,121 and 6,592,526), using a turbine system (Milner US Application 20070161893 and Feldman PCT Application US2004/012773), image processing algorithms (Sathyanarayana, WO/2003/067526) or putting the rotary drive near the distal end of the catheter to avoid the need for an elongate torque cable (Lancee, U.S. Pat. No. 5,375,602). It is advantageous to consider novel means to of compensating or reducing the effect of NURD when contemplating the implementation of novel imaging systems that involve a torque cable or other rotational element to effect scanning of the imaged tissue.

Optical coherence tomography (OCT) generally has superior resolution to ultrasound and has the potential to better identify some structures or components in vascular and other tissues. Meanwhile, ultrasound has the ability to better penetrate through biological media such as blood and soft tissues and has a depth of penetration that typically extends several millimeters beyond that of optical coherence tomography. The ability to image with either or both methods of imaging using a combined imaging device provides advantages with respect to selecting the required resolution and depth of penetration. Improvements in estimating or measuring rotational motion along an imaging probe may help enable the accurate co-registration of images when more than one imaging modality is used (such as IVUS and OCT).

Angioscopy, endoscopy, bronchoscopy and many other imaging devices have also been described which allow for the visualization of internal conduits and structures (such as vessels, gastrointestinal lumens and the pulmonary system) in mammalian bodies based on the principle of illuminating a region within the body near the distal end of a rigid or flexible shaft. Images are then created by either having a photodetector array (such as a CCD array) near the end of the shaft or by having a bundle of fiber optics transmit the received light from the distal end of the shaft to the proximal end where a photodetector array or other system is located that allows the operator to generate or look at an image representative of the illuminated region. Fiber bundles are bulky and reduce the flexibility of the shaft among other disadvantages. One of the challenges of imaging with optical means is that the presence of blood either within the imaging device or external to the imaging device can substantially reduce image quality.

A thesis written by Harm Ten Hoff ("Scanning Mechanisms for Intravascular Ultrasound Imaging: A Flexible Approach" at Erasmus University, Rotterdam, Netherlands, 1993) describes several approaches for minimizing NURD. Some of the factors listed as being important for creating a flexible rotation transmission line with a high degree of angular fidelity include i) low friction, ii) rotation symmetrical properties of the drive-shaft, iii) low bending rigidity and iv) high torsional rigidity. While in principal, low friction is desired, there will often be some friction between the drive shaft and the structures that surround it, such as a sheath.

Variations in the friction between the drive shaft and surrounding structures are a significant cause of NURD. For example, as a drive shaft rotates within a sheath, imperfections in the surfaces of the sheath, the drive shaft or a component attached to the drive shaft (such as an ultrasound transducer or housing) cause variations in the rotational friction between the rotating elements and the non-rotating elements. Rotational inertia is yet another cause of NURD when the torque cable is experiencing rotational acceleration or rotational deceleration.

Therefore, it would be very advantageous to provide catheter based imaging devices which require rotational motion of the sensors in the catheter sheath that improves transmission of torque along a rotational drive shaft.

SUMMARY OF THE INVENTION

The present invention provides means for minimizing undesired artifacts, such as non-uniform rotational distortion, in the rotational velocity near the distal end of a minimally invasive medical device. Such devices would include an imaging probe which undergoes rotational movement to scan surrounding tissue in bodily lumens and cavities.

Embodiments of the present invention provide means for minimizing the effect of non-uniform rotational distortion that occurs in imaging systems that use an elongate rotary shaft.

Embodiments of the present invention provide improved control of the rotational velocity near the distal end of the imaging probe to improve the accuracy of imaging coordinates for the reconstruction of 3D imaging data when the probe includes a 3D scanning mechanism whose behavior is dependent, at least in part, on the rotational velocity of the distal end of the rotary probe.

Therefore an embodiment of the present invention provides a catheter device for insertion into bodily lumens or cavities, comprising:

a) an elongate hollow sheath having a longitudinal axis having distal and proximal end portions and an elongate midsection;

b) a functional therapeutic or diagnostic medical device mounted in the distal end portion of said elongate hollow sheath;

c) a rotational drive mechanism extending through said elongate hollow sheath from said proximal end portion to said distal end portion, said functional therapeutic or diagnostic medical device being connected to said rotational drive mechanism such that said rotational drive mechanism imparts rotational motion to said therapeutic or diagnostic medical device about said longitudinal axis within, and with respect to, said elongate hollow sheath; and d) one or more frictional components mounted in said elongate hollow sheath located generally in said distal end portion and bearing radially outwards to be in frictional contact with an inner surface of said elongate hollow sheath so that during rotation of said functional therapeutic or diagnostic medical device by said rotational drive mechanism the rotational drive mechanism operates with a higher torsional load than in an absence of said one or more frictional components thereby reducing non-uniform rotational distortion as said functional therapeutic or diagnostic medical device rotates inside said elongate hollow sheath.

A further understanding of the functional and advantageous aspects of the invention can be realized by reference to the following detailed description and drawings.

BRIEF DESCRIPTION OF THE DRAWINGS

Preferred embodiments of the invention will now be described, by way of example only, with reference to the drawings, in which:

FIG. 2 is a perspective view of a flexible imaging catheter with an adapter, conduit and imaging assembly;

FIG. 2a is a cross sectional view of the mid section of the imaging probe of FIG. 2 taken along the dotted line;

FIG. 2b is an expanded perspective view of the distal region of the imaging probe of FIG. 2;

FIGS. 3a to 3e are representative of general imaging catheter configurations described in the art where:

FIG. 3a shows one embodiment of an over-the-wire configuration for an external sheath that may be incorporated with the imaging probe if a guidewire lumen is included;

FIG. 3b shows a cross-section through the imaging probe to demonstrate the guidewire lumen configuration;

FIG. 3c shows a rapid access configuration for an external sheath that may be incorporated with the imaging probe if a guidewire lumen is included;

FIG. 3d shows a cross-section through a portion of the imaging probe that does not contain a guidewire lumen;

FIG. 3e shows a cross-section through a portion of the imaging probe that does contain a guidewire lumen;

FIGS. 4a to 4e are representative of a catheter with an elongate sheath surrounding a rotational drive shaft and a functional component, where non-uniform rotational distortion is reduced by inclusion of a frictional element near the distal end, where:

FIG. 4a shows longitudinal cross-section through a catheter constructed according to the present invention in which there is a frictional element near the distal end of the rotational drive shaft;

FIG. 4b is a cross-sectional view of the proximal section of the catheter of FIG. 4a taken along the dotted line B;

FIG. 4c is a cross-sectional view of the distal section of the catheter of FIG. 4a taken along the dotted line C where the frictional element is in contact with the inner wall of the external sheath around its entire circumference;

FIG. 4d is a cross-sectional view of the distal section of the catheter of FIG. 4a taken along the dotted line C where the frictional element is in contact with the inner wall of the external sheath at multiple points around its entire circumference;

FIG. 4e is a cross-sectional view of the distal section of the catheter of FIG. 4a taken along the dotted line C where the frictional element has multiple extensions that extend out from the cylindrical body of the frictional element to the inner surface of the external sheath;

FIGS. 5a to 5e are representative of a catheter with an elongate sheath surrounding a rotational drive shaft and a functional component, where non-uniform rotational distortion is reduced by inclusion of a frictional element at the distal end of the group of rotational elements of the catheter, where:

FIG. 5a shows a cross-section through the catheter where there is a frictional element at the distal end of the group of rotational elements of the catheter;

FIG. 5b is a cross-sectional view of the proximal section of the catheter of FIG. 5a taken along the dotted line B;

FIG. 5c is a cross-sectional view of the distal section of the catheter of FIG. 5a taken along the dotted line C where the frictional element is in contact with the inner wall of the external sheath around its entire circumference;

FIG. 5d is a cross-sectional view of the distal section of the catheter of FIG. 5a taken along the dotted line C where the frictional element is in contact with the inner wall of the external sheath at multiple points around its entire circumference;

FIG. 5e is a cross-sectional view of the distal section of the catheter of FIG. 5a taken along the dotted line C where the frictional element has multiple extensions that extend out from the cylindrical body of the frictional element to the inner surface of the external sheath;

FIG. 6a shows another embodiment of a longitudinal cross section of a probe/catheter with an elongate sheath surrounding a rotational drive shaft and a functional component, and a frictional element at the distal end of the group of rotational elements of the catheter in which the frictional element allows fluid to flow between it and the external sheath when the catheter is flushed in a proximal to distal direction of flow;

FIG. 6b shows another embodiment of a longitudinal cross section of a probe/catheter with an elongate sheath surrounding a rotational drive shaft and a functional component, and a frictional element spaced from the distal end of the rotational drive shaft in which the catheter has a flush port near the distal end and wherein the frictional element allows fluid to flow between it and the external sheath when the catheter is flushed in a proximal to distal direction of flow;

FIG. 6c shows another embodiment of a longitudinal cross section of a probe/catheter with an elongate sheath surrounding a rotational drive shaft and a functional component, and a frictional element having spherical shape located at the distal end of the group of rotational elements of the catheter;

FIG. 6d shows a longitudinal cross section of another embodiment of a probe/catheter with an elongate sheath surrounding a rotational drive shaft and a functional component, and a frictional element having spherical shape located spaced upstream from the distal end of the group of rotational elements of the catheter;

DETAILED DESCRIPTION OF THE INVENTION

Figure 1:
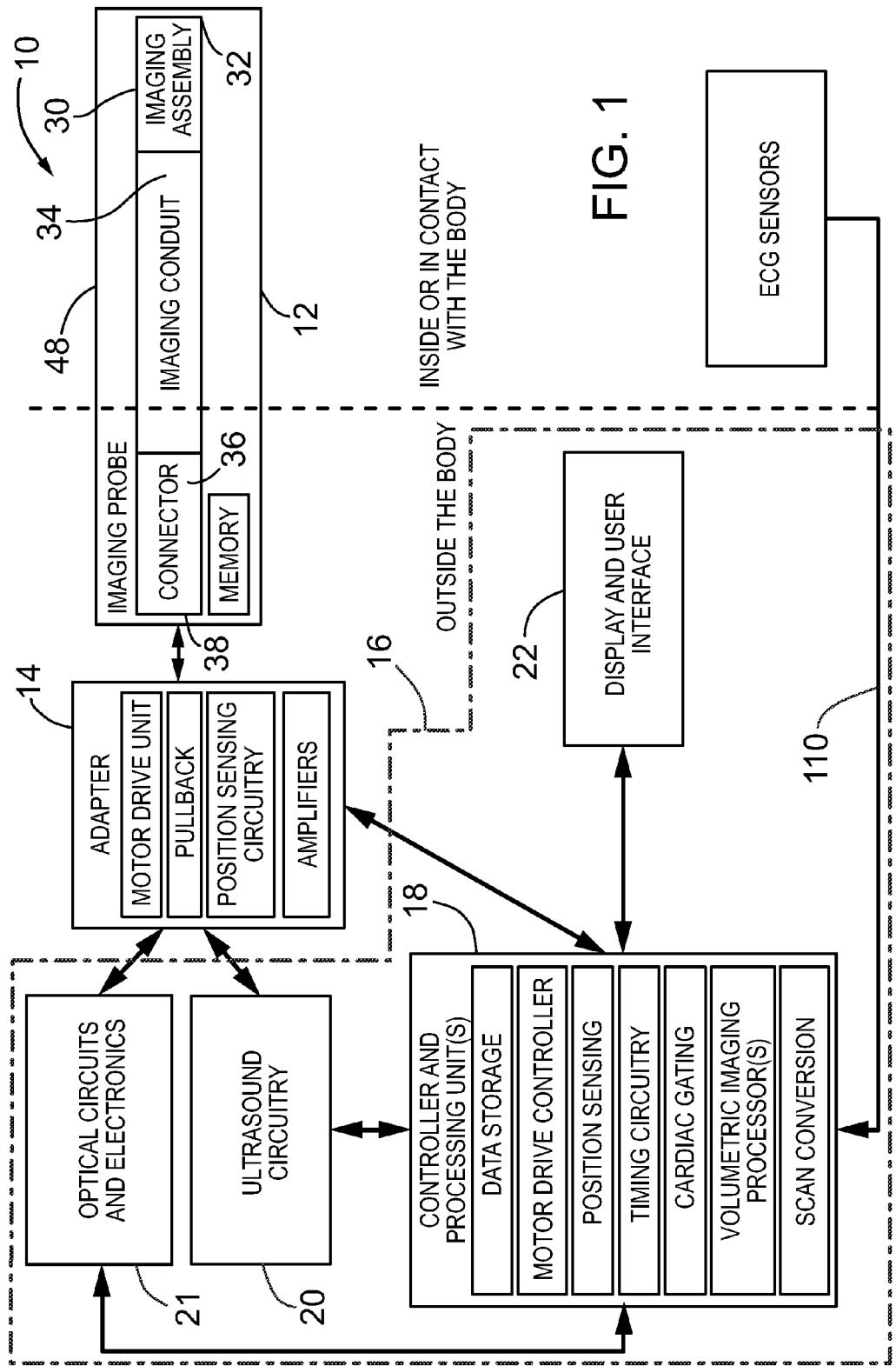
FIG. 1 is a schematic of an imaging system including ultrasound and optical imaging components.

Without limitation, the majority of the systems described herein are directed to an imaging probe using either optical or ultrasonic (or both) imaging incorporating mechanisms to reduce non-uniform rotational distortion (NURD). The imaging probe includes means for estimating a rotational motion near the distal end of a rotating shaft within the probe. As required, embodiments of the present invention are disclosed herein. However, the disclosed embodiments are merely exemplary, and it should be understood that the invention may be embodied in many various and alternative forms.

The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to an imaging probe incorporating mechanisms to reduce non-uniform rotational distortion.

As used herein, the term "about", or "approximately" when used in conjunction with ranges of dimensions, temperatures or other physical properties or characteristics is meant to cover slight variations that may exist in the upper and lower limits of the ranges of dimensions so as to not exclude embodiments where on average most of the dimensions are satisfied but where statistically dimensions may exist outside this region. For example, in embodiments of the present invention dimensions of components of an imaging probe are given but it will be understood that these are not meant to be limiting.

As used herein, the phrase "co-registration of images" refers to the process of identifying a subset of imaging data acquired by one imaging means with a subset of imaging data acquired using another imaging means where the identified imaging data from the two means was acquired by detecting a form of imaging energy (e.g. photons or ultrasound) from the same object, for example. Each co-registered point in the first subset can then be mapped to a corresponding point in the second subset such that the two points from the two different imaging means are thought to have been acquired from a similar focal region of the imaged object (or tissue).

Successful and accurate co-registration of images, or portions thereof, between images acquired using two (2) or more imaging means is helpful in that it can provide multiple opportunities to assess features of interest of the imaged object by more than one imaging means.

The present invention recognizes that variations in the friction between the rotating elements (such as the drive shaft and any tools, housings, transducers or other elements mechanically coupled to the drive shaft) and the non-rotating elements that surround the rotating elements (such as a sheath) are a more important cause of NURD than the extent of friction itself. Indeed, adding some friction near the distal end of the drive shaft can potentially reduce NURD by adding a pre-load to the rotational shaft, thus increasing the torsional rigidity of the drive shaft during operation. It can also reduce NURD during deceleration of the rotating components by assisting with deceleration of the distal portion of the drive shaft. One or more frictional elements may also act as dampening or centering elements that reduce vibrations of the rotating elements within a sheath. By using a sufficient number of the frictional elements unwanted vibrations along the drive shaft may be reduced. By reducing vibrations of the rotating elements within a sheath, the amount of friction between the rotating elements and the sheath will remain more constant.

Preferably, the torsional rigidity would not vary with longitudinal translation of the rotating elements within the sheath. Preferably, the entire length of the rotating assembly within the catheter, including the most distal extent of the rotating assembly that might include any rotating functional elements as described further below would benefit from the induction of improved torsional rigidity to reduce non-uniform rotational distortion. In some embodiments, it may be preferable to provide a sealing mechanism to prevent degradation of performance of the functional elements of the catheter due to undesired backflow of material such as blood into the lumen of the device.

Broadly, the embodiments described in the present invention are capable of reducing non-uniform rotational distortion in medical devices wherein a rotational drive shaft resides within an elongate hollow sheath such as the sheath of a catheter. Without limiting the scope of the present invention, the torque is typically applied at a proximal end of a rotary shaft while the site at which there is a functional element, such as an imaging element or a therapeutic tool is typically near a distal end of the shaft. For example, the rotary shaft for an imaging probe for minimally invasive use is mechanically coupled to a motor drive unit that resides outside of the patient.

The rotary motion of the motor drive unit and the proximal end of the rotary shaft can be measured or estimated with fairly good precision using currently available rotary encoders, such as optical encoders, magnetic encoders, resistive encoders and several others well known in the art. The output of these encoders may be used to provide input to a controller to help control the speed of the motor drive unit and the proximal end of the rotary shaft. However, the loss of ideal transmission of torque along the length of the shaft can result in changes in the rotary motion along the length of the shaft. Typically, the further distally along the rotary shaft, the less closely the rotary motion at that point will match the motion of the proximal end of the shaft. In the case of an imaging probe, this leads to non-uniform rotational distortion (NURD).

Size constraints are imposed by both the size of anatomical structures and a desire to minimize trauma during delivery and use of the imaging probe. For example, coronary arteries are typically 2-5 mm in diameter and most catheters or devices conventionally inserted into such vessels are between 0.25 to 2.5 mm in diameter. Furthermore, it is desirable for such imaging probes and therapeutic devices to be flexible in order to navigate the tortuosity of the coronary vasculature.

In general, the longer a rotational drive shaft, or the smaller the diameter the drive shaft, the more likely that NURD will occur.

Other devices into which rotational drive shafts might be incorporated would include minimally invasive imaging probes, atherectomy devices, steering probes, energy-delivery devices (such as for localized delivery of radiation, radiofrequency ablation, thermal energy, cooling probes, therapeutic ultrasound or light energy) and minimally invasive surgical devices. The majority of these devices are single-use in nature to prevent the likelihood of transmission of infectious diseases and to ensure reliable product performance. Single-use devices have more significant limitations in terms of the cost at which they can be made compared to reusable devices or probes.

FIG. 1 represents an overview of an exemplary imaging system constructed in accordance with the present invention shown generally at 10. It comprises an imaging probe 12, which connects via an adapter 14 to an image processing and display system 16. The image processing and display system 16 comprises the necessary hardware to support one or more of the following imaging modalities: 1) ultrasound, 2) optical coherence tomography, 3) angioscopy, 4) infrared imaging, 5) near infrared imaging, 6) Raman spectroscopy-based imaging and 7) fluorescence imaging.

Implementations of the optical coherence tomography, ultrasound, angioscopy and infrared imaging circuitry have been described in the prior art.

The system herein described further typically comprises a controller and processing unit 18 to facilitate the coordinated activity of the many functional units of the system, and may further comprise a display and/or user interface and may further comprise electrode sensors to acquire electrocardiogram signals from the body of the patient being imaged. The electrocardiogram signals may be used to time the acquisition of imaging data in situations where cardiac motion may have an impact on image quality. The optical circuits and electronics 21 forming image processing and display system, if included in a particular implementation of the present invention, may include any or all of the following components: interferometer components, one or more optical reference arms, optical multiplexors, optical demultiplexors, light sources, photodetectors, spectrometers, polarization filters, polarization controllers, timing circuitry, analog to digital converters and other components known to facilitate any of the optical imaging techniques described in the background and prior art sections. The ultrasound circuitry 20 may include any or all of the following components: pulse generators, electronic filters, analog to digital converters, parallel processing arrays, envelope detection, amplifiers including time gain compensation amplifiers and other components known to facilitate any of the acoustic imaging techniques described in the background and prior art sections.

The controller and processing units 18, if included in a particular implementation of the present invention, serve multiple purposes and the components would be markedly adapted based on the needs of a particular imaging system. It could include one or a combination of motor drive controller, data storage components (such as memory, hard drives, removable storage devices, readers and recorders for portable storage media such as CDs and DVDs), position sensing circuitry, timing circuitry, cardiac gating functionality, volumetric imaging processors, scan converters and others. A display and user interface 22 is also optionally provided for either real time display or display of data at a time later than the time at which imaging data is acquired.

The imaging probe 12 comprises an imaging assembly 30 near its distal end 32, an optional conduit 34 along a substantial portion of its length, and a connector 36 at its proximal end 38. For the purposes of this invention, an imaging assembly 30 generally refers to the component of the imaging probe 12 from which the signals (acoustic or optical (or both)) are collected for the purposes of imaging a region that is proximate to the imaging assembly 30. The imaging assembly 30 includes at least one or more emitters of imaging energy and at least one or more receivers of imaging energy. For the purposes of this invention, "imaging energy" refers to both light and acoustic energy. Specifically, light refers to electromagnetic waves that span the ultraviolet, visible and infrared spectrum of wavelengths. For example, for acoustic imaging, the imaging assembly 30 contains an ultrasound transducer that is both an emitter and receiver of acoustic energy.

For optical imaging, the imaging assembly 30 typically contains the distal tip of a fiber optic, as well as a combination of optical components such as a lens (such as a ball lens or GRIN lens), which collectively serve the purpose of acting as an optical receiver and may also serve as an optical emitter. A mirror and/or a prism are often incorporated as part of an optical emitter and/or receiver. The imaging assembly 30, connector 36 and/or imaging conduit 34 may be liquid-filled, such as with saline and may be flushed.

The imaging probe 12 may contain ports at one or more points along its length to facilitate flushing. For optical imaging, it is possible to consider a gas filled imaging probe 12. Preferably, the gas would substantially comprise carbon dioxide or another readily dissolved gas. Alternatively, the imaging assembly may be compartmentalized such that there is at least one gas-filled compartment or lumen for optical imaging and at least one fluid-filled compartment or chamber for acoustic imaging.

The imaging conduit 34 comprises at least one optical waveguide or at least one conductive wire (preferably two or more) that connects an emitter and/or receiver via a connector to an adapter. The imaging conduit 34 may also act as a mechanical force transmission mechanism for rotating or translating the imaging assembly. For example, the imaging conduit 34 may comprise a fiber optic, wrapped by two layers of electrical wire that are insulated by each other. The imaging conduit 34 may further be reinforced by other structural features, such as helically wrapped wires or other designs used to construct imaging torque cables for rotating scan mechanisms, as described in the prior art.

The adapter 14 facilitates transmission of signals within any fibers and/or wires to the appropriate image processing units. The adapter 14 may also incorporate a pullback mechanism 49 (FIG. 2d) or a reciprocating push-pull mechanism to facilitate longitudinal translation of the imaging assembly. Such longitudinal translation of the imaging assembly 30 may occur in conjunction with the longitudinal translation of an external shaft that surrounds the imaging conduit 34, or may occur within a relatively stationary external shaft.

Additional sensors may be incorporated as part of the adapter 14, such as position sensing circuitry, for example to sense the angle of rotation of a rotary component within the imaging probe 12. The imaging probe 12 may also include a memory component such as an EEPROM or other programmable memory device that includes information regarding the imaging probe to the rest of the imaging system. For example, it may include specifications regarding the identification of specifications of the imaging probe 12 and may also include calibration information regarding the probe 12.

While precise alignment of the acoustic and optical imaging data is highly desired, it is also important to recognize the need to optimize the geometry of a minimally invasive probe so that it is as small as reasonably possible to achieve its desired purpose. Current IVUS probes are approximately 0.9 to 2 mm in diameter and the smaller sizes of probes can be delivered more distally within the vascular tree of the coronary anatomy as the vessel size tapers down. Thus, smaller sizes generally allow for interrogation of a larger portion of the coronary anatomy.

FIG. 2 is a perspective view of a flexible imaging catheter containing a fiber optic 40 and a co-axial electrical wire 50. The proximal connector contains fiber optic 40 that can be received by the adapter to optically couple the imaging fiber optic 40 to the optical imaging system "back-end". There are also electrical connectors 56 that allow the one or more electrical conduits to be connected to the ultrasound circuitry and/or controller and processing units.

In embodiments where the imaging conduit rotates around its longitudinal axis, there may be a need to couple the rotating components of the imaging fiber optic with the relatively stationary fiber optic that connects to the optical imaging system's back-end. The coupling of a rotating fiber optic probe can be accomplished using a fiber optic rotary joint incorporated either as part of the proximal connector 36 of the imaging probe 12 or as part of the adapter 14. Similarly, in embodiments where the imaging conduit rotates around its longitudinal axis, there may be a need to couple the conductive wires that rotate with the imaging conduit with the relatively stationary conductors of the ultrasound circuitry and/or controller and processing units, preferably by means of slip rings. These slip rings can be incorporated as part of the proximal connector 36 of the imaging probe 12 or as part of the adapter 14.

FIG. 2a shows a cross sectional view of the mid section of the imaging probe of FIG. 2 taken along the dotted line which shows a fiber optic 40, guidewire port 44 and guide wire 42, imaging conduit 34, imaging conduit lumen 46, external sheath 48 which is a hollow, flexible elongate shaft made of a physiologically compatible material and having a diameter suitable to permit insertion of the hollow elongate shaft into bodily lumens and cavities, and coaxial electrical wiring 50. The expanded detailed view of the end of the imaging probe 12 shown in FIG. 2b shows the distal end of the guidewire 42 extended beyond the end of the outer sheath 48 and a flush port 54 near the end of the sheath 48. In FIG. 2 the proximal end of the imaging probe 12 includes another guidewire port 55 into which guidewire 42 is inserted and the connector assembly 36 which includes a flush port 58 and electrical contacts 56 along the connector body.

Figure 2C:
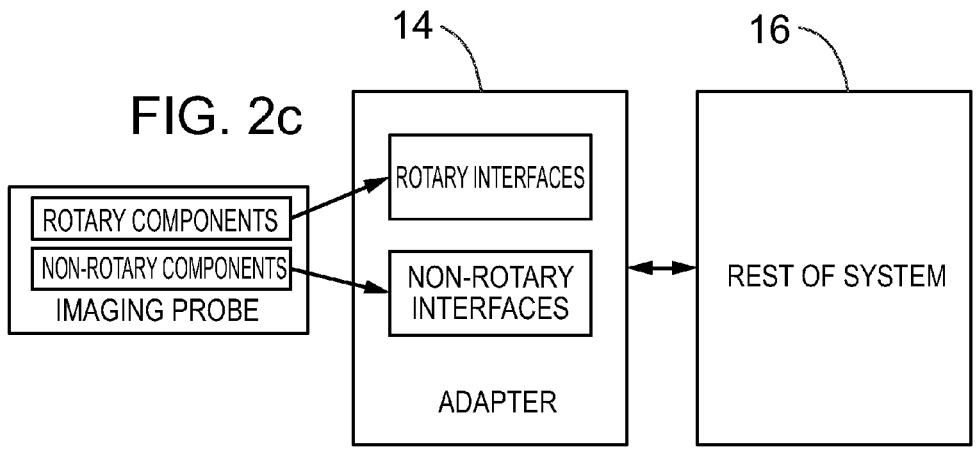
FIG. 2c shows a schematic of how the rotary and non-rotary components of the imaging probe can be coupled with an adapter to the rest of an imaging system.
Figure 2D:
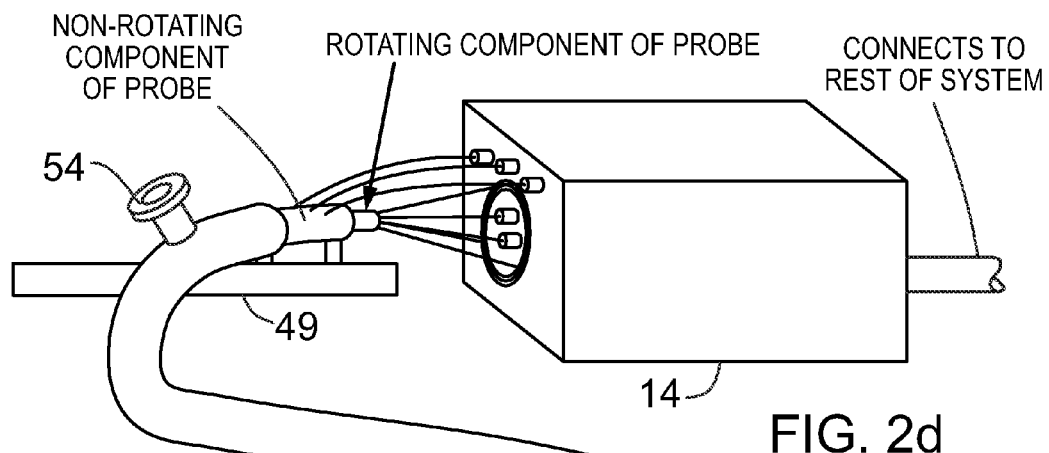
FIG. 2d is a perspective view of an example of the coupling of the rotary and non-rotary components of the probe to an adapter.

FIG. 2c shows a schematic of how the rotary and non-rotary components of the imaging probe can be coupled with an adapter to the rest of an imaging system. FIG. 2d is a perspective view of how the rotating and non-rotating components of the probe is coupled to the adapter. The rotating components of each can be electrically, optically and/or mechanically coupled using connectors and other configurations known in the art. Similarly, the non-rotating components of the imaging probe can be coupled to the non-rotating components of the adapter 14. The adapter 14 can include slip rings, optical rotary joints and other such implements for electrically or optically coupling a rotary component to a non-rotary component and enable communication of necessary electrical and optical signals with the rest of the system.

Dual-fiber optical rotary joints are also available but considerably more complex. Electrical coupling between any conductor mounted onto a rotating component in the imaging probe 12 can be coupled to non-rotating conducting elements via metallic slip rings and springs, metallic slip rings and brushes or other commonly known methods of forming conductive contact between a stationary conductor and a rotary conductor.

While the electrical, optical and mechanical connections are shown separately in FIG. 2d, it is possible to reduce the several connectors that must each be separately connected between the probe and adapter with fewer connectors by combining several connectors into combined connectors, as needed for a specific embodiment.

FIG. 3a shows one embodiment of an over-the-wire configuration for an external sheath (shown at 47) and FIG. 3b shows a cross-section of sheath 48 through the portion that contains the imaging assembly 30 along the vertical line 3b-3b in FIG. 3a.

FIG. 3c shows an embodiment at 60 that is a "rapid exchange" configuration for the external sheath that may be incorporated with the imaging probe if a guidewire is required. Sheath 48 in FIG. 3c includes the entry port 55 shown in FIG. 2. FIG. 3d shows a cross-section of the "rapid-exchange" configuration 60 through the portion that is proximal to the entry port 55 for a guidewire along line 3d-3d in FIG. 3c. FIG. 3e shows a cross-section along line 3e-3e in FIG. 3c.

Current torque cables can limit the flexibility of an imaging probe and consume valuable space within the implementation of the probe and do not fully address the problem as NURD artifacts are often still observed in IVUS imaging probes that use specially designed torque cables. Non-uniform rotational distortion gets worse as the torque cables get longer or if they are made with smaller diameters.

The reduction of non-uniform rotational distortion may be helpful for accurate co-registration of images by imaging probes that image in more than one direction from the longitudinal axis at a time. For example, it is possible to consider imaging assemblies 30 that image with ultrasound in one direction and OCT in another direction from approximately the same point along the length of the imaging probe 12. As the imaging assembly 30 rotates, regions imaged by the ultrasound transducer and the OCT system will overlap, but the imaging data at any point in time between the two imaging modalities will be imaged at different rotational angles. A reduction in NURD will improve the accuracy of the process of co-registering the ultrasound and OCT images onto each other by helping to reduce the effects of NURD.

One of the strategies generally employed to reduce non-uniform rotational distortion is to reduce friction between the rotational components and its non-rotational surroundings, such as the inner surface of the hollow shaft. By minimizing time-variations in friction between rotating and non-rotating elements of the catheter, such as between the drive shaft and the inner surface of an external sheath, there has been some success in reducing NURD. Some examples of these undesired sources of friction come from vibrations in the drive shaft causing time variations in the amount of contact between the rotating and non-rotating surfaces, asymmetries in the design of rotating components and defects in the surfaces of both the rotating and non-rotating components.

While minimizing overall friction is helpful in many regards, the more important determinant of whether or not significant NURD occurs is whether or not there is significant variation in the friction experienced over time or over the length of the rotational drive shaft and the associated rotating components. More specifically, as variations in friction over a relevant time interval cause significant changes in the torsional strain of the rotational drive shaft, NURD will worsen. A relevant time interval in the context of the present invention refers to a time interval over which the rotational performance of the drive shaft affects overall performance of the system. For an imaging catheter, a relevant time interval refers to the time in which the drive shaft is intended to travel a significant arc, such as from one thousandth of a revolution to ten revolutions, and more specifically such as from one hundredth of a revolution to one full revolution.

Non-uniform rotational distortion can be reduced by applying a pre-load to a torque cable along either its entire length, or along a significant portion of its length, so that as the rotating components experience variations in the amount of undesired friction produced between them and their non-rotating surroundings, the torque cable undergoes less rotational strain as a result of these undesired sources of friction. This pre-load can be achieved by creating one or more intentional sources of rotational friction at one or more points along the longitudinal extent of the rotating components.

Therefore, a main principle behind the present invention is that creating some friction can improve NURD by causing the torque cable to have a pre-load. This intentional friction should ideally be created in a manner such that the amount of friction is effectively uniform at a given angular velocity regardless of the angular position of the distal end of a rotary drive shaft and regardless of longitudinal translation of the rotating components within the sheath. The use of direct contact of the frictional element with the inner surface of the sheath provides an opportunity to create a greater amount of friction than simply providing a tight clearance between the sheath and the rotating components. The use of a distinct frictional element other than the torque cable (i.e. drive shaft) itself provides greater flexibility in material and geometry selection, and hence more control over properties of the frictional interface between the sheath and the frictional component. It also provides opportunity to select materials and designs of the frictional element that minimize degradation of the sheath or rotating components during the course of operation. It also provides an opportunity to select materials and designs of the frictional element that may dampen vibrations of the rotating components during operation.

FIG. 4a shows a cross-section of a catheter 100 with a rotational drive shaft 102 (which contains the imaging conduit) that is coupled to a torque source 104 (such as a motor). A significant portion of the rotational drive shaft 102 resides within a hollow shaft 106, such as an external sheath of an imaging probe. A functional element 108 resides remote from the proximal end of the rotational drive shaft 102 and is mechanically affixed to the distal end of rotational drive shaft 102. In many embodiments, such as for most imaging probes, the rotational drive shaft 102 will also include elements for enabling imaging from an imaging assembly (not shown) at the distal end of the drive shaft. For example, there may be one or more electrical conductors or one or more optical fibers within the rotational drive shaft 102. In many applications, the functional element 108 will be an imaging assembly, such as an ultrasound transducer or a collection of optical components to enable optical imaging. The imaging assembly may also include a housing to contain the ultrasound transducer or optical components. In other embodiments, the functional element 108 may be the head of an atherectomy catheter.

The functional element 108 in most embodiments will be at the distal end of the rotational drive shaft 102, but can reside anywhere along the length of the rotational drive shaft 102 remote from the proximal end. In other embodiments, there may be a plurality of functional elements 108 which may be spaced apart from each other along the longitudinal axis of the device.

A frictional element 110 is mechanically coupled to the rotary drive shaft 102 and the external sheath 106. The inner surface of the external sheath 106 can be coated with an optional coating to produce a desired amount of friction between the frictional element 110 mechanically coupled to the rotary drive shaft 102 and the external sheath 106. For example TEFLON may provide a surface with less friction. Alternatively, materials that tend to attract to each other via electrostatic interactions may increase the friction between the rotational and non-rotational components exerted by the frictional element 110. Alternatively, the frictional element 110 itself may have a coating that changes its properties.

As seen in FIG. 4b, around most of the circumference of the rotational components and along most of the length of the rotational drive shaft 102 will be a clearance between the rotating components and their surroundings. Typically, this clearance ranges from 5 microns to 1 millimeter and more typically ranges from 25 microns to 200 microns. Larger clearance results in less friction, but can worsen other issues related to device performance such as creating unwanted vibrations.

FIG. 4a shows the frictional element 110 remote to the proximal end of the rotational drive shaft 102 where the frictional element 110 is in contact with the inner surface of the external sheath 106 that surrounds the rotating components. The friction between the frictional element 110 and its surroundings cause the rotational drive shaft 102 to operate with a higher torsional load than it would otherwise operate (or a "pre-load").

This pre-load helps allow the desired rotational motion of the functional element 108 at the distal end of the device to be more closely achieved by minimizing the significance of sources of undesired friction that occur over time along the length of the rotational drive shaft 102.

Note that the external sheath 106 in this embodiment and most others can be substituted with any lumen in which a rotational drive shaft 102 resides, such as in a lumen of a gastrointestinal endoscope or a vascular catheter.

It is important that the frictional element 110 create friction that is substantially uniform over the course of a full rotation. In order for this to occur, the frictional element 110 would preferably be symmetric about the longitudinal axis of the rotational drive shaft 102. Material selection and sizing of the frictional element 110 are important in achieving the desired amount of friction and will vary substantially between embodiments.

Generally, the frictional element 110 can be made of any one or more materials commonly used in medical devices, including polymers and soft or compressible materials such as polyethylenes, vinyls, silicones, nylons, PEBAX, teflon, foam and several others. The frictional element 110 can be made by any combination of several processes known in the art including injection molding, dip molding, machining, coating, stereolithography, extrusion, cutting, laser cutting, grinding and others. Hard materials can also be used in the composition of the frictional elements 110, such as polycarbonates, metals, ceramics and others, although it may be desirable to ensure the frictional surfaces of such elements 110 are well polished or otherwise made smooth.

The frictional component (or element—the two terms are used interchangeably herein but mean the same thing) 110 can be incorporated as an intrinsic feature of one of the rotating components, such as the rotational drive shaft 102 or the functional element 108.

It may also be desirable to provide channels for fluid communication between the regions distal and proximal to the frictional element. One possibility is to incorporate channels in the frictional element 120 shown in FIG. 4c. FIG. 4d shows an alternative embodiment of a frictional component 130 wherein the frictional element 130 is shaped to have multiple contacts 132 around its circumference between the frictional component 130 and the inner surface of the external sheath 106. Fluid communication is allowed in the gaps 134 between the points of contact 132 so that fluid may flow between the regions distal and proximal to the frictional component 130.

FIG. 4e shows an alternative embodiment of a frictional component 140 wherein the frictional element 140 has one or more flexible extensions 142 that radiate from the cylindrical body which surrounds the rotational drive shaft 102. These flexible extensions 142 have a relatively large surface contact with the inner surface of the external sheath 106. Friction in this embodiment may be derived more so from electrostatic or similar cohesive forces between the materials of the extensions and the inner sheath rather than friction created by normal forces between the extensions and the inner sheath.

FIGS. 5a to 5e show embodiments of a probe 150 with frictional components 160 which are very similar to FIGS. 4a to 4e, with the exception that the frictional component 160 is the most distal rotational component, and thus does not substantially surround another rotational component such as the rotational drive shaft 102 or a functional component 108.

FIG. 6a shows an embodiment of a probe 180 with a frictional component 182 attached to the distal end of the functional element 108 wherein the frictional component 182 has thin walls that make direct contact with the inner surface of the external sheath 106. The frictional component may be made of a somewhat compressible material so that as fluid is flushed in a proximal to distal direction through the lumen of the external sheath, the thin walls of the frictional component 182 can temporarily release their contact with the inner surface of the sheath, thus allowing fluid to flow through the lumen and exit the flush port 184 shown. In this embodiment, the frictional element 182 also acts as a one-way valve, which may inhibit blood or other foreign matter from entering into the lumen of the sheath. In other embodiments, this optional valving function may be obviated by introducing optional fenestrations into the thin walls of the frictional component 182.

FIG. 6b shows yet another embodiment of a probe 186 where the thin walled frictional element 182 is spaced back from the distal end of the rotational drive shaft rather than being located at the distal end of the functional element as shown in FIG. 6a.

FIGS. 6c and 6d show probes similar to those of FIGS. 6a and 6b with the difference being the frictional elements 182' are substantially spherical in shape. The main advantage of this spherical shape is that the friction applied by a frictional element 182' of this shape will be less affected than other shapes, such as a cylindrical shape, when the sheath gets curved during use in tortuous anatomy.

For all of the embodiments above, the frictional forces exerted by the frictional element on the structures that surround the rotating components, such as the external sheath, would preferably not cause damage or significantly deform the surrounding structures. It may be necessary in same cases to reinforce the surrounding structures. For example, the external sheath might need to have increased torsional rigidity to withstand the forces transmitted from the rotational drive shaft to the sheath through the frictional element. Such reinforcement may be accomplished by increasing the wall thickness of the external sheath, by making the diameter of the sheath larger, by selecting more rigid materials, or by reinforcing the sheath with other components such as wire braiding, as is commonly practiced in the art of manufacturing medical catheters.

Figure 7A:
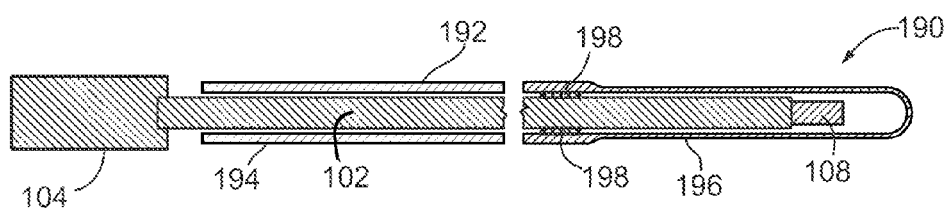
FIG. 7a shows a longitudinal cross section of another embodiment of a probe/catheter with an elongate sheath surrounding a rotational drive shaft and a functional component in which the external sheath has increased torsional rigidity along its proximal and mid sections, compared to its distal section and configured such that the frictional component creates friction between the drive shaft and the external sheath proximal to the distal region of the external sheath.

An alternative embodiment of a probe, shown generally at 190 in FIG. 7a has an external sheath 192 with a proximal section 194 that is mechanically reinforced, as shown by the thicker wall for the sheath. The frictional element 198 is located along the rotational drive shaft 102 at a point that is within or proximate to the distal end of the reinforced proximal section 194 of the external sheath 192. The distal region 196 of the external sheath 192 is not reinforced and is thus able to be smaller in diameter or made of softer or more flexible materials, which can be advantageous for delivering the distal region of the device to tortuous and/or small anatomic locations, such as coronary vessels. Even though a lesser portion of the length of the rotational drive shaft is pre-loaded by the frictional element 198, the amount of NURD allowed by the proximal section of the rotational drive shaft will be reduced, and will allow substantial reduction in the likelihood and severity of NURD experienced by the functional element 108.

Figure 7B:
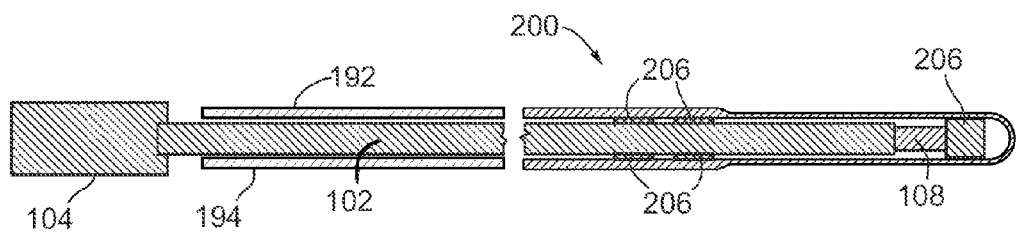
FIG. 7b shows a longitudinal cross section of another embodiment of a probe/catheter with an elongate sheath surrounding a rotational drive shaft, a functional component and a plurality of frictional elements along the length of the drive shaft.

Yet another embodiment of a probe, shown generally at 200 in FIG. 7b wherein there are multiple frictional elements 206 along the length of the rotational drive shaft 102. This distributes the frictional force transmitted from the rotational drive shaft 102 to several points along the length of the external sheath 106. Such embodiments may be mechanically advantageous in avoiding damage or deformation to the external sheath or other surrounding structures while allowing adequate pre-loading of the torque cable along its entire length to achieve the desired reduction in NURD and while enabling a sufficiently flexible and miniaturized distal region of the external sheath.

Figure 7C:
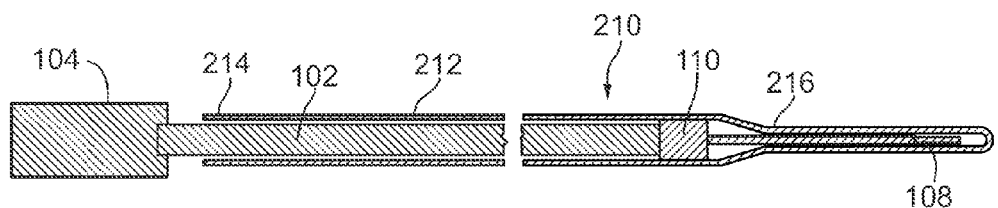
FIG. 7c shows a longitudinal cross section of another embodiment of a probe/catheter with an elongate sheath surrounding a rotational drive shaft, a functional component and a frictional element to create friction between the external sheath and the rotational drive shaft, and in which the rotational drive shaft has a wider diameter in its proximal and mid sections, and a smaller diameter in its distal section such that the frictional element in FIG. 7C also serves as a coupling mechanism to mechanically couple the different sizes of rotational drive shaft seen herein.

Yet another embodiment is shown at 210 in FIG. 7c wherein the inner and outer diameters or the distal portion 216 of the external sheath 212 is more significantly reduced than the proximal portion 214 or shown in other embodiments illustrated.

Another embodiment involves incorporating the frictional element as part of the functional element. For example, an ultrasound transducer as a functional element may be embedded within a frictional element that is made of an acoustically transparent material. Such materials include PEBAX, nylon and many others known in the art. Similarly, an optical emitter/receiver, such as a prism and lens assembly at the distal end of a fiber, may be embedded within a frictional element that is made of optically transparent material, again, such as PEBAX, nylon and many other materials known in the art.

The present invention provides embodiments of rotatable catheters for insertion into bodily lumens which incorporate friction devices to improve transmission of torque along a rotational drive shaft within the catheter, and these embodiments meet the need for higher fidelity torque transmission during use of the torque cable for uses when the rotational velocity of the torque cable is varied over time.

If dynamic drag is induced by the outer sheath either necking down or having an inner protrusion onto the torque cable (such as disclosed in U.S. Pat. No. 4,951,677 issued to Crowley et al.) then the amount of torsional strain induced at the distal end of the torque cable will vary if the torque cable is longitudinally translated within the sheath. By having the drag-inducing component attached to the torque cable at a constant position in the torque cable such as disclosed herein, the amount of strain induced at the distal end will not vary with longitudinal translation of the torque cable within the sheath.

In addition, the contact of the frictional component against the inner wall of the outer sheath in embodiments disclosed herein will allow achievement of a higher and more constant degree of torsional strain.

In many embodiments disclosed herein, the contact of the frictional component against the inner wall of the outer sheath in will allow for a seal to take place, inhibiting blood from entering into the lumen of the sheath via any holes in the sheath such as flush port 184. The interface between the frictional component and the sheath can act as a valve where fluid introduced into the lumen of the sheath at adequate pressure will be able to squeeze between the frictional component and the sheath, thus allowing the lumen to be flushed, but the seal will be of adequate integrity that the physiological pressures of fluids external to the catheter transmitted to the sheath lumen via a flush port (ie. the systolic and diastolic pressures in a vessel) will be below the amount of pressure required to overcome the sealing effect of the frictional component. Blood/foreign substances can compromise image integrity, so this sealing effect is of use.

Embodiments of the invention use several frictional elements along the length of the device and other embodiments use different diameters of the sheath and torque cable in combination with the one or more frictional elements.

The use of a soft or compressible material for the frictional element to make contact with the inner wall of the sheath is very advantageous. This provides less trauma/wear to the inner sheath than the torque cable. The use of a frictional component that is distinct from the torque cable, such as disclosed herein, provides more flexibility in design of material properties that create the friction.

The use of a soft or compressible material for the one or more frictional element may also provide a dampening effect that minimizes vibrations of the rotating elements within the sheath, thus providing a more constant degree of friction between the rotational elements and the inner wall of the sheath.

Integration into an Imaging Probe

The frictional elements disclosed herein may be incorporated into an imaging probe 12 of FIGS. 1 to 3 by substituting the functional end of any of the embodiments in FIGS. 4 to 7 for an imaging assembly 30 and substituting the rotary drive shaft for an imaging conduit 34 suitable for carrying either electrical or optical signals. In many embodiments of imaging probes it is desirable to slide the imaging conduit 34 (which can also act as a torque transmission shaft) and the imaging assembly 30 within the external sheath. The translating along the longitudinal axis of the imaging probe 12 is referred to as a "pullback" and is commonly done to enable imaging of different regions of tissue found along a portion of the imaging probe 12 without having to move the external sheath 48.

Several embodiments for improving the performance of a rotational drive shaft 102 have been shown in the description of the present invention.

Referring to FIG. 1 again, imaging probe 12 (which may include any of the embodiments of the acoustic and optical sensors discussed herein) and its components may be of several dimensions and properties depending on the anatomic location and purpose of use for the imaging that is enabled by the imaging probe 12. For example, for the purposes of use in the cardiovascular system, including the cardiac chambers, the imaging probe 12 would preferably be elongate and flexible, with a length ranging from 5 to 3000 mm, preferably with a length ranging from 300 mm to 1600 mm. The imaging conduit 34 and imaging assembly 30 may have a maximum cross-sectional dimension ranging from 200 microns to 10 mm, preferably ranging from 500 microns to 5 mm. An external sheath 48 may surround both the imaging conduit 34 and imaging assembly 30. This would enable the imaging conduit 34 and imaging assembly 30 to rotate within the external sheath while mechanically isolating the rotational motion of these two components from the surrounding tissues.

In yet another example, the use of the imaging probe 12 in the gastrointestinal system would typically have the imaging probe 12 being elongate and flexible, with a length ranging from 100 mm to 2000 mm and preferably in the range of 300 mm to 1500 mm. The maximum cross-sectional dimension would typically range from 3 mm to 20 mm.

In yet another example, the use of the imaging probe 12 to image soft tissue via percutaneous means would have the imaging probe with a rigid shaft. The external sheath 48 would be replaced by a rigid hollow shaft, such as a stainless steel tube although many other metals, polymers and even ceramics would be functionally suitable.

Embodiments of the present invention can be used in conjunction with or incorporated into devices that are used for intervention, such as those used for cardiovascular intervention, such as an angioplasty balloon, atherectomy device, stent delivery system or localized drug delivery system. It can also be used in conjunction with or incorporated into devices that facilitate biopsies, radio-frequency ablation, resection, cautery, localized brachytherapy, cryotherapy, laser ablation or acoustic ablation.

In particular, using the image scanning mechanism to direct higher powers of optical or acoustic energy to a targeted region can facilitate the use of the current device to enable laser or acoustic ablation of tissue. For example, while imaging a region of a blood vessel with an OCT or ultrasound embodiment of an imaging probe 12 described in the present invention a region for the delivery of therapy can be selected through a user interface. Then, powerful pulses of energy can be delivered at times when the scanning mechanism is oriented to delivery energy in the desired direction. For example, pulses of laser energy can be transmitted down the same fiber optic used for optical imaging, be deflected by a deflecting component in those embodiments that include a deflecting component, and travel towards the targeted tissue for the desired effect. The timing of the pulses of laser energy is coordinated with the scanning pattern affected by the imaging probe 12 to direct the energy towards the targeted region.

Gastrointestinal endoscopy, colposcopy, bronchoscopy, laparoscopy, laryngoscopy, cystoscopy, otoscopy and fundoscopy are all examples of applications to which the scanning mechanisms described in the present invention may be adapted for use in a manner similar to angioscopy or infrared imaging. Non-medical uses of a flexible and/or miniaturizable imaging probe where a scanning mechanism described in this invention is used to produce an image, such as a picture taken in the visible or infrared spectrum are several.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A catheter device for insertion into bodily lumens or cavities, comprising:
   an elongate hollow sheath having a distal end portion, a proximal end portion, and an elongate midsection;
   a rotational drive shaft housed within said elongate hollow sheath;
   a functional element mounted to said rotational drive shaft at a location that is remote from said proximal end portion of said elongate hollow sheath; and
   at least one frictional component operatively associated with at least one of said rotational drive shaft and said functional element, such that said frictional component bears radially outwards to be in frictional contact with an inner surface of said elongate hollow sheath;
   said frictional component being configured such that an amount of frictional force produced by contact between said frictional component and said inner surface of said elongate hollow sheath is uniform regardless of the angular orientation and longitudinal translation of the rotating components within said hollow elongate sheath;
   said frictional component being configured such that the contact between said frictional component and said inner surface of said elongate hollow sheath is independent of the angular orientation and longitudinal translation of the rotating components within said hollow elongate sheath; and
   such that during rotation of said functional element by said rotational drive shaft, said rotational drive shaft is configured to operate with a higher torsional load than in an absence of said frictional component, thereby reducing non-uniform rotational distortion as said functional element rotates inside said elongate hollow sheath.

2. The catheter device according to claim 1 wherein said at least one frictional component comprises one or more generally cylindrical frictional components circumferentially enveloping a portion of said rotational drive shaft, said generally cylindrical frictional components having a radially outwardly projecting portion which bears against the inner surface of said elongate hollow sheath.

3. The catheter device according to claim 2 wherein said at least one generally cylindrical frictional component comprises a plurality of such components spaced along a length of said rotational drive shaft.

4. The catheter device according to claim 2 wherein said at least one generally cylindrical frictional component comprises one or more cylindrical members having an inner radius approximately equal to an outer radius of the rotational drive shaft, and has an outer radius approximately equal to an inner radius of the elongate hollow sheath.

5. The catheter device according to claim 2 wherein said at least one frictional component comprises one or more cylindrical members having an inner radius approximately equal to an outer radius of the rotational drive shaft, wherein the one or more cylindrical members have an outer circumference shaped for making multiple contacts around its circumference between the one or more frictional components and the inner surface of the elongate hollow sheath.

6. The catheter device according to claim 2 wherein said at least one cylindrical frictional component comprises one or more cylindrical members having an inner radius approximately equal to an outer radius of the rotational drive shaft, wherein the cylindrical members comprise one or more flexible extensions radiating therefrom.

7. The catheter device according to claim 1 wherein said at least one frictional component comprises one or more generally cylindrical frictional components that circumferentially envelops said functional element, wherein said generally cylindrical frictional components have a portion that extends radially from said functional element and bears against the inner surface of said elongate hollow sheath.

8. The catheter device according to claim 7 wherein said one or more generally cylindrical frictional components comprise a plurality of such components spaced along said functional element.

9. The catheter device according to claim 7 wherein said one or more generally cylindrical frictional components comprise one or more cylinders having an inner radius approximately equal to an outer radius of the functional element, and has an outer radius approximately equal to an inner radius of the elongate hollow sheath.

10. The catheter device according to claim 7 wherein said one or more cylindrical frictional components comprise one or more cylinders having an inner radius approximately equal to an outer radius of the functional element, wherein the frictional component has an outer circumference shaped for making multiple contacts around its circumference between each frictional component and the inner surface of the elongate hollow sheath.

11. The catheter device according to claim 7 wherein said one or more cylindrical frictional components are one or more cylindrical members having an inner radius approximately equal to an outer radius of the functional element, wherein the one or more cylindrical frictional components comprise one or more flexible extensions radiating therefrom, each flexible extension having a relatively large surface contact with the inner surface of the elongate hollow sheath.

12. The catheter device according to claim 1 wherein said at least one frictional component is a generally spherically shaped and flexible component circumferentially enveloping a portion of said rotational drive shaft, having a radius such that an outer circumference of said spherically shaped component radially bears against the inner surface of said elongate hollow sheath.

13. The catheter device according to claim 1 wherein said at least one frictional component comprises a soft or compressible material so that as fluid is flushed in a proximal to distal direction through the lumen of the hollow elongate sheath, walls of the one or more frictional components can temporarily release their contact with the inner surface of the sheath, thus allowing fluid to flow through the lumen and exit from a distal end portion of the elongate hollow sheath.

14. The catheter device according to claim 13 including fenestrations built into walls of the frictional component to assist fluid passage past the frictional component.

15. The catheter device according to claim 1 wherein said functional element is generally cylindrical in shape, and wherein said frictional component is a generally spherically shaped member circumferentially enveloping said functional element, having a radius such that an outer circumference of said spherically shaped component radially bears against the inner surface of said elongate hollow sheath.

16. The catheter device according to claim 1 wherein said functional element is an imaging assembly configured for emitting an energy beam and receiving reflected energy signals.

17. The catheter device according to claim 1 wherein said functional element is selected from the group consisting of minimally invasive imaging probes, atherectomy devices, steering probes, energy-delivery devices for localized delivery of radiation, radiofrequency ablation, thermal energy, cooling probes, therapeutic ultrasound or light energy and minimally invasive surgical devices.

18. The catheter device according to claim 3 wherein said plurality of components spaced along said length of said rotational drive shaft are sufficient to damp vibrations of said functional element and said rotational drive shaft.

19. The catheter device according to claim 1 wherein said frictional component is configured to permit fluid flow between regions distal and proximal thereto while said frictional component is in contact with said inner surface of said elongate hollow sheath.

20. The catheter device according to claim 19 wherein said frictional component is further configured to permit fluid flow unidirectionally.

21. The catheter device according to claim 1 wherein the frictional force resulting from the frictional contact is effectively uniform at a given angular velocity.

22. The catheter device according to claim 1 wherein said frictional component is remote from the proximal end of the rotational drive shaft.

23. The catheter device according to claim 1 wherein the frictional component is proximate to the functional element.

* * * * *